(12) United States Patent
Ogiwara et al.

(10) Patent No.: US 8,961,929 B2
(45) Date of Patent: Feb. 24, 2015

(54) TARGETING AGENT FOR TUMOR SITE

(75) Inventors: Kazutaka Ogiwara, Ashigarakami-gun (JP); Makoto Ohno, Ashigarakami-gun (JP); Masayoshi Kojima, Ashigarakami-gun (JP); Masayuki Kawakami, Ashigarakami-gun (JP); Chihaya Kakinuma, Ashigarakami-gun (JP); Tasuku Sasaki, Ashigarakami-gun (JP); Kiyohito Takada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/520,827

(22) PCT Filed: Jan. 7, 2011

(86) PCT No.: PCT/JP2011/050178
§ 371 (c)(1),
(2), (4) Date: Jul. 6, 2012

(87) PCT Pub. No.: WO2011/083845
PCT Pub. Date: Jul. 14, 2011

(65) Prior Publication Data
US 2013/0017147 A1    Jan. 17, 2013

(30) Foreign Application Priority Data
Jan. 8, 2010  (JP) ................. 2010-002696

(51) Int. Cl.
*A61K 51/08*   (2006.01)
*A61K 49/00*   (2006.01)

(52) U.S. Cl.
CPC ......... *A61K 49/0034* (2013.01); *A61K 49/0063* (2013.01); *A61K 49/0084* (2013.01)
USPC ........................................ 424/1.69; 514/17.2

(58) Field of Classification Search
None
See application file for complete search history.

(56) References Cited

U.S. PATENT DOCUMENTS

| | | | |
|---|---|---|---|
| 5,013,556 A | 5/1991 | Woodle et al. | |
| 5,593,622 A | 1/1997 | Yoshioka et al. | |
| 5,676,971 A | 10/1997 | Yoshioka et al. | |
| 5,846,458 A | 12/1998 | Yoshioka et al. | |
| 6,992,172 B1 | 1/2006 | Chang et al. | |
| 7,517,954 B2 | 4/2009 | Bouwstra et al. | |
| 7,560,427 B2 | 7/2009 | Bouwstra et al. | |
| 7,579,314 B2 | 8/2009 | Bouwstra et al. | |
| 7,598,347 B2 | 10/2009 | Bouwstra et al. | |
| 7,645,737 B2 | 1/2010 | Bouwstra et al. | |
| 7,671,016 B2 | 3/2010 | Bouwstra et al. | |
| 7,976,868 B2 * | 7/2011 | Thorpe | 424/450 |
| 8,080,515 B2 | 12/2011 | Bouwstra et al. | |
| 8,138,139 B2 | 3/2012 | Bouwstra et al. | |
| 2003/0194373 A1 * | 10/2003 | Fauconnier et al. | 424/1.69 |
| 2006/0241032 A1 | 10/2006 | Bouwstra et al. | |
| 2008/0113910 A1 | 5/2008 | Bouwstra et al. | |
| 2008/0114078 A1 | 5/2008 | Bouwstra et al. | |
| 2008/0167446 A1 | 7/2008 | Bouwstra et al. | |
| 2008/0274957 A1 | 11/2008 | Bouwstra et al. | |
| 2009/0182063 A1 | 7/2009 | Bouwstra et al. | |
| 2010/0048477 A1 | 2/2010 | Bouwstra et al. | |
| 2010/0222264 A1 | 9/2010 | Bouwstra et al. | |
| 2012/0156132 A1 * | 6/2012 | Nakamura et al. | 424/1.69 |

FOREIGN PATENT DOCUMENTS

| | | | | |
|---|---|---|---|---|
| JP | H2149512 | | 6/1990 | |
| JP | 5-501264 | A | 3/1993 | |
| JP | H5506040 | | 9/1993 | |
| JP | 7-20857 | B2 | 3/1995 | |
| JP | 2667051 | B2 | 10/1997 | |
| JP | 2007528699 | A | 10/2007 | |
| JP | 2007-297402 | A | 11/2007 | |
| JP | 2007535909 | A | 12/2007 | |
| JP | 2009203174 | | 9/2009 | |
| WO | 91/05546 | A1 | 5/1991 | |
| WO | 9610394 | | 4/1996 | |
| WO | 2004085473 | A2 | 10/2004 | |
| WO | 2005054293 | A1 | 6/2005 | |
| WO | 2007/088952 | A1 | 8/2007 | |
| WO | 2008/103041 | A1 | 8/2008 | |
| WO | WO 2008 103041 | * | 8/2008 | ............. A61K 38/39 |
| WO | WO 2008 103042 | * | 8/2008 | ............. A61K 38/39 |
| WO | 2009040811 | A2 | 4/2009 | |
| WO | 2009108686 | | 9/2009 | |

OTHER PUBLICATIONS

International Search Report for PCT/JP2011/050178 dated Apr. 26, 2011.
International Preliminary Report on Patentability and Written Opinion received in International Patent Application PCT/JP2011/050178.
Office Action issued in counterpart Japanese Patent Application No. 2011-549033, mailed Feb. 12, 2014.
Office Action for Japanese Application No. 2011-549033 dated Dec. 22, 2014.

\* cited by examiner

*Primary Examiner* — Karlheinz R Skowronek
*Assistant Examiner* — Mindy Newman
(74) *Attorney, Agent, or Firm* — Sughrue Mion, PLLC

(57) ABSTRACT

It is an object of the present invention to provide a targeting agent, which enables the delivery of a drug to tumor sites or the imaging of tumor sites by utilizing its effect of accumulating to such tumor sites. The present invention provides a targeting agent for tumor site, which comprises a hydrophilic polymer-modified carrier coated with a gelatin-like protein that has repeats of a sequence represented by Gly-X-Y characteristic to collagen and has two or more sequences of cell adhesion signals in a single molecule wherein X and Y each independently represent an amino acid and a plurality of Gly-X-Y sequences may be the same or different.

15 Claims, 1 Drawing Sheet

R-Gel-coated ICG-containing PEGylated liposome
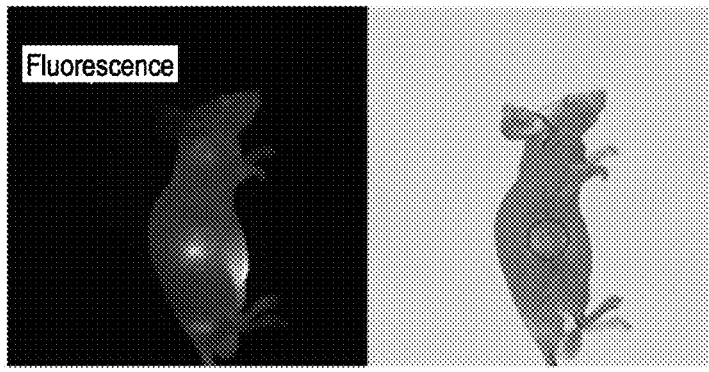
Animal gelatin-coated ICG-containing PEGylated liposome
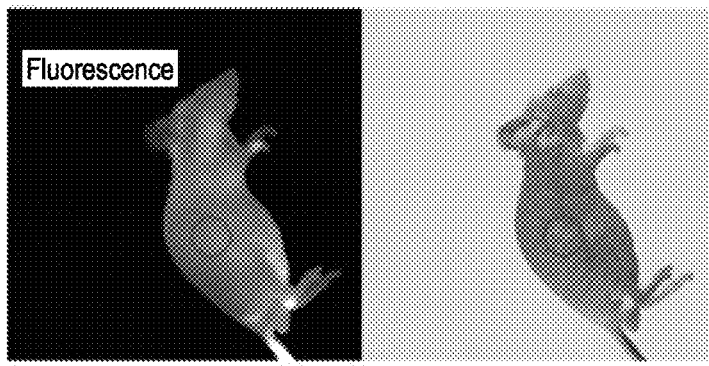
ICG-containing PEGylated liposome
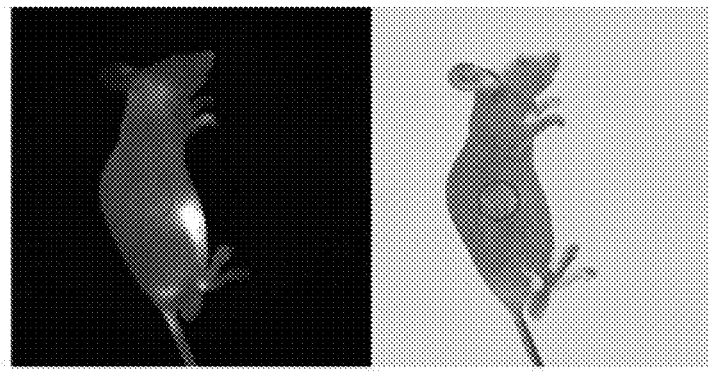
Tumor site: circled

SEQUENCE LISTING

<160> NUMBER OF SEQ ID NOS: 1

<210> SEQ ID NO 1
<211> LENGTH: 571
<212> TYPE: PRT
<213> ORGANISM: Artificial Sequence

```
<220> FEATURE:
<223> OTHER INFORMATION: Synthetic peptide

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
            85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
        130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
            165                 170                 175

Asp Gly Ala Pro Gly Lys Asp Gly Val Arg Gly Leu Ala Gly Pro Pro
            180                 185                 190

Gly Ala Pro Gly Leu Gln Gly Ala Pro Gly Leu Gln Gly Met Pro Gly
        195                 200                 205

Glu Arg Gly Ala Ala Gly Leu Pro Gly Pro Lys Gly Glu Arg Gly Asp
        210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
            245                 250                 255

Glu Arg Gly Asp Ala Gly Pro Lys Gly Ala Asp Gly Ala Pro Gly Lys
            260                 265                 270

Asp Gly Val Arg Gly Leu Ala Gly Pro Ile Gly Pro Pro Gly Glu Arg
        275                 280                 285

Gly Ala Ala Gly Leu Pro Gly Pro Lys Gly Glu Arg Gly Asp Ala Gly
        290                 295                 300

Pro Lys Gly Ala Asp Gly Ala Pro Gly Lys Asp Gly Val Arg Gly Leu
305                 310                 315                 320

Ala Gly Pro Ile Gly Pro Pro Gly Pro Ala Gly Ala Pro Gly Ala Pro
            325                 330                 335

Gly Leu Gln Gly Met Pro Gly Glu Arg Gly Ala Ala Gly Leu Pro Gly
            340                 345                 350

Pro Lys Gly Glu Arg Gly Asp Ala Gly Pro Lys Gly Ala Asp Gly Ala
        355                 360                 365

Pro Gly Lys Asp Gly Val Arg Gly Leu Ala Gly Pro Pro Gly Ala Pro
        370                 375                 380

Gly Leu Gln Gly Ala Pro Gly Leu Gln Gly Met Pro Gly Glu Arg Gly
385                 390                 395                 400
```

```
Ala Ala Gly Leu Pro Gly Pro Lys Gly Glu Arg Gly Asp Ala Gly Pro
            405             410             415

Lys Gly Ala Asp Gly Ala Pro Gly Ala Pro Gly Leu Gln Gly Met Pro
            420             425             430

Gly Glu Arg Gly Ala Ala Gly Leu Pro Gly Pro Lys Gly Glu Arg Gly
        435             440             445

Asp Ala Gly Pro Lys Gly Ala Asp Gly Ala Pro Gly Lys Asp Gly Val
    450             455             460

Arg Gly Leu Ala Gly Pro Ile Gly Pro Pro Gly Glu Arg Gly Ala Ala
465             470             475             480

Gly Leu Pro Gly Pro Lys Gly Glu Arg Gly Asp Ala Gly Pro Lys Gly
            485             490             495

Ala Asp Gly Ala Pro Gly Lys Asp Gly Val Arg Gly Leu Ala Gly Pro
            500             505             510

Ile Gly Pro Pro Gly Pro Ala Gly Ala Pro Gly Ala Pro Gly Leu Gln
        515             520             525

Gly Met Pro Gly Glu Arg Gly Ala Ala Gly Leu Pro Gly Pro Lys Gly
    530             535             540

Glu Arg Gly Asp Ala Gly Pro Lys Gly Ala Asp Gly Ala Pro Gly Lys
545             550             555             560

Asp Gly Val Arg Gly Leu Ala Gly Pro Pro Gly
            565             570
```

TARGETING AGENT FOR TUMOR SITE

CROSS REFERENCE TO RELATED APPLICATIONS

This application is a National Stage of International Application No. PCT/JP2011/050178 filed Jan. 7, 2011, claiming priority based on Japanese Patent Application No. 2010-002696 filed Jan. 8, 2010, the contents of all of which are incorporated herein by reference in their entirety.

TECHNICAL FIELD

The present invention relates to a targeting agent for tumor site, which comprises a carrier coated with a gelatin-like protein.

BACKGROUND ART

Many drugs have been developed for cancer therapy. However, an antitumor agent, which selectively exhibits a cell-killing effect only on tumor tissues, has not yet been developed to date. When an antitumor substance is directly administered into a blood vessel, the substance promptly disappears from the blood, and it is distributed even in organs other than the target organ. Thus, a majority of such antitumor substances cannot exhibit a sufficient antitumor activity on cancerous tissues. In addition, these antitumor substances have undesired action on normal tissues (side effect) and cause significant toxicity. Accordingly, the enhancement of the antitumor activity of antitumor substances and reduction in side effects are important subjects for cancer chemotherapy, and it has been strongly desired to develop a Drug Delivery System (DDS) for efficiently accumulating a drug in cancerous tissues and cancer cells.

Liposome is a closed vesicle comprising, as a main ingredient, a biological component-derived phospholipid. The liposome is characterized in that it exhibits low toxicity and low antigenicity when it is administered to a living body. Moreover, it has been shown that the stability in blood and biological distribution of a drug are changed by encapsulating the drug in a liposome, and that as a result, the accessibility of the drug to the target tissues can be improved. Furthermore, it has also been known that the blood vessel walls of new blood vessels often appearing in cancerous tissues have permeability higher than that of the existing blood vessels, and that vesicles such as liposome are likely to accumulate in the cancerous tissues. Accordingly, a liposome medicament is one of DDS, which is highly anticipated to enhance antitumor activity and reduce side effects.

However, when a liposome medicament containing an antitumor substance is used for cancer therapy, an ordinary liposome composition has only an insufficient property of selectively reaching cancerous tissues, and thus, the antitumor effect of the antitumor substance cannot be sufficiently exhibited in many cases. Moreover, such a liposome medicament is also problematic in that side effects appear as a result of distribution of a large amount of liposome in organs other than the target organ. Hence, the aforementioned problems are intended to be solved by two approaches, namely, passive DDS and active DDS.

Passive DDS is a method, which comprises modifying a liposome with a hydrophilic polymer such as polyethylene glycol to impart a high blood retention property to the liposome, so as to allow the liposome to accumulate in tissues with increased blood vessel permeability, such as tumor tissues and inflammatory sites (see Patent Document 1 and Patent Document 2). As a modifier used for modifying a membrane with a hydrophilic polymer, a polyethylene glycol derivative formed by binding a phospholipid, a cholesterol or the like to polyethylene glycol (PEG) is generally used.

Active DDS is a method, which comprises physically or chemically modifying a lipid membrane of liposome with a peptide, protein or antibody having a property of selectively aggregating to cancerous tissues, so as to increase the transitivity of the liposome to the cancerous tissues. As a peptide with affinity for tumor tissues, there is well-known a peptide, which specifically transfers to integrin that is hardly present in normal tissues and is specifically expressed in new blood vessels in tumor and which binds thereto. Representative examples of such a peptide includes peptides comprising an RGD sequence. It has been reported that these peptides selectively bind to integrins $\alpha v\beta 3$ and $\alpha v\beta 5$, which are expressed in new blood vessels in tumor. However, when a lipid membrane of liposome has been modified with only these peptides, the obtained effects have been insufficient in many cases, although selective transitivity to cancerous tissues and an increased antitumor effect have been observed. Furthermore, in many cases, the types of animal species and cancers, in which antitumor effects have been recognized, have been limited. Although the type of a peptide and the modification level have been changed in various ways, the increased level of the antitumor effect has been restricted. Accordingly, it is considered that there is a high hurdle to jump to develop a drug available in clinical sites. For example, in Patent Document 3, a liposome is modified using a peptide containing 3 to 15 amino acids. In this technique, however, accumulation ability has not been sufficient. In addition, a liposome whose surface has been modified with a sugar chain accumulating in cancer is not sufficient, either, in terms of accumulation ability.

On the other hand, biological polymers, such as gelatin, have been widely used to date as medical materials. With recent advances in genetic engineering, recombinant proteins have been produced by introducing various genes in *Escherichia coli* or yeast. By this genetic engineering, various types of recombinant collagen-like proteins have been synthesized (Patent Documents 4 and 5). When compared with natural gelatin, these recombinant collagen-like proteins have excellent non-infectivity and uniformity. Moreover, the recombinant collagen-like proteins are also advantageous in that, since their sequences have been determined, the strength and degradability thereof can be designed precisely. Patent Document 6 discloses that a sequence which contains many RGD sequences is useful as a drug delivery agent. However, this document does not suggest that the combination of such a sequence with a liposome is useful.

PRIOR ART DOCUMENTS

Patent Documents

Patent Document 1: JP Patent Publication (Kokoku) No. 7-20857 B (1995)
Patent Document 2: Japanese Patent No. 2667051
Patent Document 3: International Publication WO2007/088952
Patent Document 4: U.S. Pat. No. 6,992,172
Patent Document 5: International Publication WO2008/103041
Patent Document 6: JP Patent Publication (Kokai) No. 2007-297402 A

SUMMARY OF INVENTION

Object to be Solved by the Invention

It is an object of the present invention to develop a carrier having two functions, namely, a high blood retention property and a property of selectively aggregating to cancerous tissues, so as to provide a targeting agent, which enables the delivery of a drug to tumor sites or the imaging of tumor sites by utilizing its effect of accumulating to such tumor sites.

Means for Solving the Object

As a result of intensive studies directed towards achieving the aforementioned object, the present inventors have found that a carrier, which is formed by coating a PEGylated liposome with a gelatin-like protein, such as a recombinant gelatin having an amino acid sequence derived from a partial amino acid sequence of a collagen, is accumulated in tumor sites, thereby completing the present invention.

Thus, the present invention provides a targeting agent for tumor site, which comprises a hydrophilic polymer-modified carrier coated with a gelatin-like protein that has repeats of a sequence represented by Gly-X-Y characteristic to collagen and has two or more sequences of cell adhesion signals in a single molecule wherein X and Y each independently represent an amino acid and a plurality of Gly-X-Y sequences may be the same or different.

Preferably, the hydrophilic polymer-modified carrier is a liposome containing a lipid membrane component modified with a hydrophilic polymer, or a polymer micelle modified with a hydrophilic polymer.

Preferably, the molecular weight of the gelatin-like protein is 2 KDa to 100 KDa.

Preferably, the molecular weight of the gelatin-like protein is 10 KDa to 90 KDa.

Preferably, the gelatin-like protein is represented by the formula:

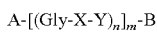

A-[(Gly-X-Y)$_n$]$_m$-B wherein A represents any amino acid or amino acid sequence, B represents any amino acid or amino acid sequence, there exist n amino acids each independently represented by X, there exist n amino acids each independently represented by Y, n represents an integer from 3 to 100, m represents an integer of 2 to 10, and n Gly-X-Y sequences may be the same or different.

Preferably, the gelatin-like protein is represented by the formula:

Gly-Ala-Pro-[(Gly-X-Y)$_{63}$]$_3$-Gly wherein there exist 63 amino acids each independently represented by X, there exist 63 amino acids each independently represented by Y, and 63 Gly-X-Y sequences may be the same or different.

Preferably, the cell adhesion signal is an amino acid sequence represented by Arg-Gly-Asp.

Preferably, the amino acid sequence of the gelatin-like protein does not comprise any of serine and threonine.

Preferably, the amino acid sequence of the gelatin-like protein does not comprise any of serine, threonine, asparagine, tyrosine and cysteine.

Preferably, the amino acid sequence of the gelatin-like protein does not comprise an amino acid sequence represented by Asp-Arg-Gly-Asp.

Preferably, the gelatin-like protein has (1) the amino acid sequence shown in SEQ ID NO: 1, or (2) an amino acid sequence having 80% or more homology to the amino acid sequence shown in SEQ ID NO: 1 and having targeting activity on a tumor site.

Preferably, the gelatin-like protein is crosslinked.

Preferably, the crosslinking is carried out using an aldehyde, a condensing agent or an enzyme.

Preferably, the hydrophilic polymer is polyethylene glycol.

Preferably, the targeting agent of the present invention is an imaging agent that targets to a tumor site.

Preferably, the targeting agent of the present invention is a drug delivery agent that targets to a tumor site.

Preferably, the targeting agent of the present invention further comprises a labeled probe and/or a drug.

Preferably, the labeled probe is a fluorescent dye, a radioisotope, a nuclide used for PET, a nuclide used for SPECT, an MRI contrast medium, a CT contrast medium, or a magnetic material.

Preferably, the fluorescent dye is a quantum dot, indocyanine green, or a near-infrared fluorescent dye; each of the radioisotope, the nuclide used for PET, and the nuclide used for SPECT is $^{11}$C, $^{13}$N, $^{15}$O, $^{18}$F, $^{66}$Ga, $^{67}$Ga, $^{68}$Ga, $^{60}$Cu, $^{61}$Cu, $^{62}$Cu, $^{67}$Cu, $^{64}$Cu, $^{48}$V, Tc-99m, $^{241}$Am, $^{55}$Co, $^{57}$Co, $^{153}$Gd, $^{111}$In, $^{133}$Ba, $^{82}$Rb, $^{139}$Ce, Te-123m, $^{137}$Cs, $^{86}$Y, $^{90}$Y, $^{185/188}$Re, $^{186/188}$Re, $^{125}$I, or a complex thereof, or a combination thereof; and each of the MRI contrast medium, the CT contrast medium, and the magnetic material is gadolinium, Gd-DTPA, Gd-DTPA-BMA, Gd-HP-DO3A, iodine, iron, iron oxide, chromium, manganese, a complex or chelate complex thereof, or a combination thereof.

The present invention further provides a method for targeting a labeled probe and/or drug to a tumor site, which comprises administering to a living body, a hydrophilic polymer-modified carrier which is coated with a gelatin-like protein that has repeats of a sequence represented by Gly-X-Y characteristic to collagen and has two or more sequences of cell adhesion signals in a single molecule wherein X and Y each independently represent an amino acid and a plurality of Gly-X-Y sequences may be the same or different, wherein the carrier further comprises the labeled probe and/or the drug.

The present invention further provides a use of a hydrophilic polymer-modified carrier coated with a gelatin-like protein that has repeats of a sequence represented by Gly-X-Y characteristic to collagen and has two or more sequences of cell adhesion signals in a single molecule wherein X and Y each independently represent an amino acid and a plurality of Gly-X-Y sequences may be the same or different, for the production of a targeting agent for tumor site.

Effect of the Invention

The targeting agent for tumor site of the present invention enables the delivery of a drug to tumor sites or the imaging of tumor sites by utilizing its effect of accumulating to such tumor sites. The targeting agent for tumor site of the present invention has two functions, namely, a high blood retention property and a property of selectively aggregating to cancerous tissues.

BRIEF DESCRIPTIONS OF DRAWINGS

FIG. 1 shows the results of an experiment, in which an R-Gel-coated ICG-containing PEGylated liposome, an animal gelatin-coated ICG-containing PEGylated liposome, or an ICG-containing PEGylated liposome has been administered into the caudal vein of a cancer-bearing animal, and in which a fluorescence imaging experiment has been then performed ex vivo.

EMBODIMENTS FOR CARRYING OUT THE INVENTION

Hereinafter, the embodiment of the present invention will be described in detail.

(1) Hydrophilic Polymer-Modified Carrier

Hydrophilic polymer-modified carriers include a polymer micelle and a liposome. Of these, a liposome is preferable. Polymer micelle is an aggregate formed by associating block copolymers having two types of polymer chains with each different solubility (e.g. a hydrophobic chain and a hydrophilic chain) in a solvent. On the other hand, liposome is a closed vesicle having an internal water phase portion enclosed with a bimolecular lipid membrane formed by dispersing phospholipids in water. The liposome is classified into three types, namely, Multilamellar Vesicle (MLV), Large Unilamellar Vesicle (LUV) and Small Unilamellar Vesicle (SUV), depending on size or the number of bimolecular lipids. Any one of the aforementioned vesicles can be used as a liposome in the present invention. The liposome used in the present invention is preferably a liposome capable of stably forming a liposome structure before and after being administered into a living body.

The flowability and membrane permeability of a bimolecular membrane constituting a liposome are significantly increased when the liposome reaches a phase transition temperature. Thus, in general, it is preferable to use a phospholipid having a phase transition temperature of 37° C. or higher. Examples of such a phospholipid include hydrogenated purified egg phosphatidylcholine (phase transition temperature: 50° C.-60° C.; hereinafter referred to as "HEPC"), hydrogenated purified soybean phosphatidylcholine (phase transition temperature: approximately 55° C.; hereinafter referred to as "HSPC"), dipalmitoyl phosphatidylcholine (phase transition temperature: approximately 41° C.; hereinafter referred to as "DPPC"), and distearoyl phosphatidylcholine (phase transition temperature: approximately 58° C.; hereinafter referred to as "DSPC"). Of these, DSPC and DPPC are more preferable. These phospholipids can be used singly or in combination of two or more types. The liposome used in the preset invention may comprise a stabilizing agent such as a cholesterol derivative, which has been reported to improve the stability of a liposome, as well as the aforementioned phospholipids. The molar ratio between a cholesterol derivative and a phospholipid is preferably 1:0.3 to 3, and more preferably 1:1 to 2.5. It is also possible to add glycerin, glucose, sodium chloride or the like as an isotonizing agent to the liposome. In addition, an antiseptic agent such as a paraben-based compound, chlorobutanol, benzyl alcohol or propylene glycol may also be added to the present liposome.

The liposome used in the present invention contains a lipid membrane component modified with a hydrophilic polymer. That is to say, in the liposome used in the present invention, the outer surface of a bimolecular lipid membrane is modified with a hydrophilic polymer. The hydrophilic polymer is not particularly limited. Examples of the hydrophilic polymer include polyethylene glycol, ficoll, polyvinyl alcohol, a styrene-maleic anhydride alternating copolymer, a divinyl ether-maleic anhydride alternating copolymer, polyvinyl pyrrolidone, polyvinyl methyl ether, polyvinylmethyloxazoline, polyethyloxazoline, polyhydroxypropyloxazoline, polyhydroxypropylmethacrylamide, polymethacrylamide, polydimethylacrylamide, polyhydroxypropyl methacrylate, polyhydroxyethyl acrylate, hydroxymethyl cellulose, hydroxyethyl cellulose, polyaspartamide, and synthetic polyamino acid. Among these compounds, polyethylene glycol-based compounds, polyglycerin-based compounds and polypropylene glycol-based compounds are preferable, and polyethylene glycol (PEG), polyglycerin (PG) and polypropylene glycol (PPG) are more preferable, because these compounds have the effect of improving the blood retention property of a medicament. Furthermore, from the viewpoint of preservation stability, such a hydrophilic polymer preferably has one end that is alkoxylated (methoxylated, ethoxylated or propoxylated). Among the above-mentioned compounds, polyethylene glycol (PEG) is most commonly used as a hydrophilic polymer. PEG has the effect of improving the blood retention property of a medicament, and thus, it is particularly preferable.

The above-described hydrophilic polymer preferably has a structure for modifying a liposome. The hydrophilic polymer particularly preferably has the aforementioned structure at one end of the hydrophilic polymer chain. That is, a hydrophilic polymer to be used in modification is preferably composed of a main part of a hydrophilic polymer and a structural part for modifying a liposome. When this structure is a hydrophobic portion such as a lipid, the main part of the hydrophilic polymer is immobilized such that it protrudes from the outer surface of the liposome, so that the hydrophobic portion can be inserted into the liposome membrane. When the structure is a reactive functional group capable of binding to a liposome membrane constituent via a covalent bond, it covalently binds to the liposome membrane constituent exposed on the outer surface of the liposome, such as a phospholipid, and the main part of the hydrophilic polymer is immobilized such that it protrudes from the outer surface of the liposome.

Next, a hydrophobic compound, which is used to bind to the main part of the hydrophilic polymer so as to form a hydrophilic polymer-hydrophobic polymer compound, will be described below.

The hydrophobic compound is not particularly limited. For example, compounds having a hydrophobic region (hydrophobic compounds) can be used. Examples of such a hydrophobic compound include: phospholipids that constitute mixed lipids as described later; other lipids such as sterol; long-chain fatty-acid alcohol; and glycerin fatty acid esters. Among these compounds, phospholipids are preferable. In addition, these hydrophobic compounds may have a reactive functional group. A covalent bond is preferable as a bond formed by such a reactive functional group. Specific examples of the bond include an amide bond, an ester bond, an ether bond, a sulfide bond, and a disulfide bond. However, the type of the bond is not particularly limited.

The acyl chain contained in the above-described phospholipid is preferably a saturated fatty acid. The chain length of the acyl chain is preferably $C_{14}$-$C_{20}$, and more preferably $C_{16}$-$C_{18}$. Examples of the acyl chain include dipalmitoyl, distearoyl, and palmitoylstearoyl. The phospholipid is not particularly limited. For example, a phospholipid having a functional group capable of reacting with the above-described hydrophilic polymer can be used. Specific examples of such a phospholipid having a functional group capable of reacting with the hydrophilic polymer include: phosphatidyl ethanolamine having an amino group; phosphatidyl glycerol having a hydroxy group; and phosphatidyl serine having a carboxy group. In a preferred embodiment, the above-described phosphatidyl ethanolamine is used.

A lipid derivative of the hydrophilic polymer is composed of the above-described hydrophilic polymer and the above-described lipid. The combination of the above-described hydrophilic polymer with the above-described lipid is not particularly limited. An appropriate combination of the hydrophilic polymer with the lipid can be used, depending on purpose. An example is a derivative of the hydrophilic polymer, which is formed by binding at least one selected from among a phospholipid, another lipid such as sterol, a long-chain fatty-acid alcohol and glycerin fatty acid ester, with at least one selected from among PEG, PG and PPG A specific example of such a derivative is polyoxypropylene alkyl. In a preferred embodiment, a phospholipid or a cholesterol is selected as a lipid, particularly when the hydrophilic polymer is polyethylene glycol (PEG). Examples of a lipid derivative of PEG in such a combination include a phospholipid derivative of PEG and a cholesterol derivative of PEG.

As such a lipid derivative of the hydrophilic polymer, a positively-charged, negatively-charged, or neutral lipid derivative can be selected, depending on the type of a lipid. For example, when DSPE is selected as a lipid, the lipid derivative thereof becomes negatively charged due to the influence of a phosphate group. On the other hand, when a cholesterol is selected as a lipid, the lipid derivative thereof becomes neutral. The type of a lipid can be selected depending on purpose.

The molecular weight of PEG is not particularly limited. The molecular weight of PEG is generally 500 to 10,000 daltons, preferably 1,000 to 7,000 daltons, and more preferably 2,000 to 5,000 daltons. The molecular weight of PG is not particularly limited. The molecular weight of PG is generally 100 to 10,000 daltons, preferably 200 to 7,000 daltons, and more preferably 400 to 5,000 daltons. The molecular weight of PPG is not particularly limited. The molecular weight of PPG is generally 100 to 10,000 daltons, preferably 200 to 7,000 daltons, and more preferably 1,000 to 5,000 daltons.

Among the aforementioned substances, a phospholipid derivative of PEG is preferable. An example of such a phospholipid derivative of PEG is polyethylene glycol-distearoyl phosphatidyl ethanolamine (PEG-DSPE). PEG-DSPE is preferable because this is a commonly used compound, which is easily available.

The above-described hydrophilic polymer can be used singly or in combination of two or more types.

Such a lipid derivative of the hydrophilic polymer can be produced by a conventionally known method. An example of a method for synthesizing a phospholipid derivative of PEG, which is an example of the lipid derivatives of the hydrophilic polymer, is a method comprising allowing a phospholipid having a functional group capable of reacting with PEG to react with PEG, using a catalyst. Examples of such a catalyst include cyanuric chloride, carbodiimide, acid anhydride, and glutaraldehyde. The above-described functional group is allowed to covalently bind to PEG by performing the aforementioned reaction, so as to obtain a phospholipid derivative of PEG.

The modification rate of modifying membrane lipids (total lipids) with the above-described lipid derivative of the hydrophilic polymer can be set at generally 0.1 to 20 mol %, preferably 0.1 to 5 mol %, and more preferably 0.5 to 5 mol %, relative to the membrane lipids. The term "total lipids" is herein used to mean the total amounts of all lipids constituting membranes, other than the lipid derivative of the hydrophilic polymer. Thus, the term "total lipids" specifically includes phospholipids and other lipids. Further, when other surface modifiers are present, such surface modifiers are also included in the total lipids.

The liposome used in the present invention may comprise other membrane constituents, as well as the above-described phospholipid and the lipid derivative of the hydrophilic polymer. Examples of the other membrane constituents include lipids other than the phospholipid, and the derivatives thereof (hereinafter collectively referred to as "other lipids"). It is preferable that a liposome be formed with a membrane of mixed lipid containing other lipids, as well as with the above-described phospholipid and the lipid derivative of the hydrophilic polymer used as main membrane materials.

The liposome used in the present invention can be prepared according to a known method. In the present invention, the liposome preferably has a mean particle diameter of 50 to 200 nm.

(2) Gelatin-Like Protein

The gelatin-like protein used in the present invention has repeats of a sequence represented by Gly-X-Y characteristic to collagen and has two or more sequences of cell adhesion signals in a single molecule wherein X and Y each independently represent an amino acid and a plurality of Gly-X-Y sequences may be the same or different. As a gelatin-like protein used in the present invention, a recombinant gelatin having an amino acid sequence derived from a partial amino acid sequence of collagen can be used. Examples of a recombinant gelatin that can be used include, but are not limited to, recombinant gelatins described in EP1014176A2, U.S. Pat. No. 6,992,172, WO2004-85473, and WO2008/103041. A recombinant gelatin which is preferable as the gelatin-like protein used in the present invention is described below.

The recombinant gelatin used in the present invention has original properties of naturally occurring gelatin and thus it is highly biocompatible. In addition, the recombinant gelatin is not directly obtained from natural sources and thus has no risk of causing BSE or the like. In this regard, it has an excellent property of being non-infectious. In addition, the recombinant gelatin used in the present invention is more homogenous than naturally occurring gelatin. Further, the recombinant gelatin has a predetermined sequence. Thus, it is possible to precisely design the recombinant gelatin in terms of strength and degradability with few errors by crosslinking or the like described below.

The molecular weight of the gelatin-like protein used in the present invention is preferably 2 KDa to 100 KDa, more preferably 2.5 KDa to 95 KDa, further preferably 5 KDa to 90 KDa, and most preferably 10 KDa to 90 KDa.

Preferably, the gelatin-like protein used in the present invention contains repeats of a sequence represented by Gly-X-Y characteristic to collagen. Here, a plurality of sequences each represented by Gly-X-Y may be the same or different. Gly in Gly-X-Y represents glycine. X and Y in Gly-X-Y represent any amino acids (and preferably any amino acids other than glycine). When gelatin/collagen is compared with other proteins in terms of the amino acid composition or sequence, the GXY sequence is characteristic to collagen and forms a highly specific partial structure. Glycine accounts for approximately one-third of the partial structure as a whole. Glycine is repeatedly found in the amino acid sequence at a rate of 1 out of every 3 amino acids. Glycine is the simplest amino acid. There are few restrictions to arrangement of the molecular chain of glycine and thus glycine highly contributes to regeneration of the helix structure upon gelatinization. Preferably, an amino acid represented by X or Y is rich in imino acid (proline or oxyproline) and the imino acid accounts for 10% to 45% of the amino acid sequence as a whole. Amino acids forming the GXY repeat structure account for preferably 80% or more, more preferably 95% or more, and most preferably 99% or more of the amino acid sequence as a whole.

A generally available gelatin contains charged polar amino acids and uncharged polar amino acids at a ratio of 1:1. Here, the term "polar amino acid" specifically refers to cysteine, aspartic acid, glutamic acid, histidine, lysine, asparagine, glutamine, serine, threonine, tyrosine, or arginine. In particular, the term "uncharged polar amino acid" refers to cysteine, asparagine, glutamine, serine, threonine, or tyrosine. The percentage of polar amino acids relative to all amino acids constituting the gelatin-like protein used in the present invention is 10% to 40% and preferably 20% to 30%. In addition, the percentage of uncharged polar amino acids relative to the polar amino acids is preferably 5% to less than 20% and more preferably less than 10%. Further, the amino acid sequence does not contain one amino acid and preferably two amino acids or more selected from among serine, threonine, asparagine, tyrosine, and cysteine.

In general, it is known that a polypeptide contains a minimal amino acid sequence that functions as a cell adhesion signal sequence (e.g., "Pathophysiology" (*Byotai Seiri*) Vol. 9, No. 7 (1990), p. 527, Nagai Shoten Co., Ltd.). It is preferable for a single molecule of the gelatin-like protein used in the present invention to have at least two cell adhesion signal sequences. In view of an increase in types of adhering cells, examples of such sequence are: preferably an RGD sequence, an LDV sequence, an REDV sequence, a YIGSR sequence, a PDSGR sequence, an RYVVLPR sequence, an LGTIPG sequence, an RNIAEIIKDI sequence, an IKVAV sequence, an LRE sequence, a DGEA sequence, and an HAV sequence (the amino acids are shown by one-letter notation), more preferably an RGD sequence, a YIGSR sequence, a PDSGR sequence, an LGTIPG sequence, an IKVAV sequence, and an HAV sequence; and particularly preferably an RGD sequence. Among the RGD sequence, an ERGD sequence is preferred.

In terms of arrangement of RGD sequences in the gelatin-like protein used in the present invention, the number of amino acids present between two RGD sequences is preferably 0 to 100 and more preferably 25 to 60. Preferably, the number of amino acids is not uniformly determined.

In view of cell adhesion/growth, the number of such minimal amino acid sequences in a single protein molecule is preferably 3 to 50, more preferably 4 to 30, particularly preferably 5 to 20, and most preferably 12.

The percentage of RGD motifs in the gelatin-like protein used in the present invention related to the total number of amino acids is preferably at least 0.4%. If the gelatin-like protein comprises 350 amino acids or more, each stretch of 350 amino acids contains preferably at least one RGD motif. The percentage of RGD motifs related to the total number of amino acids is more preferably at least 0.6%, further preferably at least 0.8%, still further preferably at least 1.0%, even further preferably at least 1.2%, and most preferably at least 1.5%. The number of RGD motifs in the gelatin-like protein is preferably at least 4, more preferably 6, further preferably 8, and even further preferably 12 to 16 per 250 amino acids. A percentage of RGD motifs of 0.4% corresponds to at least one RGD sequence per 250 amino acids. The number of RGD motifs is represented by an integer. Therefore, in order to achieve a percentage of RGD motifs of 0.4%, it is necessary for a gelatin comprising 251 amino acids to contain at least two RGD sequences. Preferably, the gelatin-like protein of the present invention contains at least 2 RGD sequences per 250 amino acids, more preferably at least 3 RGD sequences per 250 amino acids, and further preferably at least 4 RGD sequences per 250 amino acids. In another embodiment, the gelatin-like protein of the present invention comprises at least 4, preferably 6, more preferably 8, and further preferably 12 to 16 RGD motifs.

In addition, the gelatin-like protein may be partially hydrolyzed.

Preferably, the gelatin-like protein used in the present invention has a structure comprising repeats of A-[(Gly-X-Y) $_n$]$_m$-B. Here, "m" is an integer of preferably 2 to 10 and more preferably 3 to 5. In addition, "n" is an integer of preferably 3 to 100, more preferably 15 to 70, and most preferably 50 to 65.

Preferably, a plurality of naturally occurring collagen sequence units are bound to form a repeat unit. The term "naturally occurring collagen" used herein may refer to any naturally occurring collagen. However, preferable examples thereof include type-I, type-II, type-III, type-IV, and type-V collagens. More preferably, type-I, type-II, and type-III collagens are used. In another embodiment, the origin of such collagen is preferably a human, bovine, pig, mouse, or rat and it is more preferably a human.

The isoelectric point of the gelatin-like protein used in the present invention is preferably 5 to 10, more preferably 6 to 10, and further preferably 7 to 9.5.

Preferably, the gelatin-like protein is not deaminated.

Preferably, the gelatin-like protein does not comprise telopeptide.

Preferably, the gelatin-like protein is a substantially pure collagen material prepared from a nucleic acid encoding a naturally occurring collagen.

Particularly preferably, the gelatin-like protein used in the present invention is a gelatin-like protein having the following (1) or (2):

(1) the amino acid sequence shown in SEQ ID NO: 1; or (2) an amino acid sequence having 80% or more (more preferably 90% or more, and most preferably 95% or more) homology to the amino acid sequence shown in SEQ ID NO: 1, and having targeting activity on a tumor site.

The gelatin-like protein (recombinant gelatin) used in the present invention can be produced by a gene recombination technique known to persons skilled in the art. For instance, it can be produced according to the method described in EP1014176A2, U.S. Pat. No. 6,992,172, WO2004/85473, or WO2008/103041. Specifically, a transformant is produced by obtaining a gene encoding the amino acid sequence of a predetermined recombinant gelatin, incorporating the gene into an expression vector to prepare a recombinant expression vector, and introducing the vector into an appropriate host. The obtained transformant is cultured in an appropriate medium to produce a recombinant gelatin. Therefore, the recombinant gelatin used in the present invention can be prepared by collecting the produced recombinant gelatin from the culture product.

The gelatin-like protein used in the present invention can be chemically modified depending on the application thereof. Chemical modification may be performed via introduction of a low molecular compound or a different polymer (e.g., a biopolymer (sugar or protein), a synthetic polymer, or polyamide) into a carboxyl group or an amino group of a side chain of the gelatin-like protein or crosslinking between gelatin-like proteins. For example, a carbodiimide-based condensing agent is used for introduction of a low molecular compound into the gelatin-like protein.

The crosslinking agent used in the present invention is not particularly limited, as long as the present invention can be carried out. It may be a chemical crosslinking agent or an enzyme. Examples of a chemical crosslinking agent include formaldehyde, glutaraldehyde, carbodiimide, and cyanamide. Preferably, formaldehyde or glutaraldehyde is used. Further, crosslinking of a gelatin can be conducted by light irradiation to a gelatin into which a photoreactive group has been introduced, light irradiation under the presence of a photosensitizer, or the like. Examples of a photoreactive group include a cinnamyl group, a coumarin group, a dithiocarbamyl group, xanthene dye, and camphorquinone.

In a case in which enzymatic crosslinking is carried out, an enzyme used is not particularly limited, as long as it has an action of causing crosslinking between gelatin-like protein chains. However, crosslinking can be carried out using preferably transglutaminase or laccase and most preferably transglutaminase. Examples of proteins that are enzymatically crosslinked by transglutaminase include, but are not particularly limited to, proteins having lysine residues and glutamine residues. A mammalian-derived or microorganism-derived transglutaminase may be used. Specific examples thereof include: the Activa series (produced by Ajinomoto Co., Inc.); commercially available mammalian-derived transglutaminases serving as reagents such as guinea pig liver-derived transglutaminase, goat-derived transglutaminase, and rabbit-derived transglutaminase (produced by Oriental Yeast Co., Ltd., Upstate USA Inc., Biodesign International, etc.); and a human-derived blood coagulation factor (Factor XIIIa, Haematologic Technologies, Inc.).

Crosslinking of the gelatin-like protein comprises the following two steps: a step of mixing a gelatin-like protein solution and a crosslinking agent; and a step of causing a reaction in the obtained homogenous solution.

According to the present invention, the mixing temperature for treating the gelatin-like protein with a crosslinking agent is not particularly limited, as long as the solution can be homogenously agitated. However, it is preferably 0° C. to 40° C., more preferably 0° C. to 30° C., further preferably 3° C. to 25° C., still further preferably 3° C. to 15° C., even further preferably 3° C. to 10° C., and particularly preferably 3° C. to 7° C.

After agitation of the gelatin-like protein and the crosslinking agent, the temperature can be increased. The reaction temperature is not particularly limited, as long as crosslinking can proceed. However, in view of denaturation or degradation of the gelatin-like protein, it is substantially 0° C. to 60° C., preferably 0° C. to 40° C., more preferably 3° C. to 25° C., further preferably 3° C. to 15° C., still further preferably 3° C. to 10° C., and particularly preferably 3° C. to 7° C.

The method of coating a carrier with a gelatin-like protein may be either a method involving a chemical bond, or a method involving an electrostatic interaction. In order to avoid denaturation of a carrier membrane, etc., the method involving an electrostatic interaction is preferable.

The molar ratio between the phospholipid used in the present invention and the total amount of a gelatin-like protein is preferably 1:0.01 to 0.3, more preferably 1:0.05 to 0.2, and particularly preferably 1:0.1.

(3) Intended Use and Usage of the Targeting Agent for Tumor Site of the Present Invention According to the present invention, the above-described gelatin-like protein (particularly preferably, a recombinant gelatin) is administered to a subject (e.g. a mammal such as a human), so that a substance can be targeted to a tumor site. That is to say, according to the present invention, since a gelatin-like protein targets to a tumor site and accumulates therein, a desired substance can be delivered to the tumor site as a target. Accordingly, the targeting agent for tumor site of the present invention can be used as an imaging agent targeting to a tumor site, for example, and it can also be used as a drug delivery agent targeting to a tumor site.

When the targeting agent for tumor site of the present invention is used as an imaging agent targeting to a tumor site, the targeting agent can comprise a labeled probe. In addition, when the targeting agent for tumor site of the present invention is used as a drug delivery agent targeting to a tumor site, the targeting agent can comprise a drug (a therapeutically effective ingredient). Moreover, if necessary, the targeting agent can comprise both a labeled probe and a drug (a therapeutically effective ingredient).

Examples of a labeled probe used when the targeting agent of the present invention is used as an imaging agent include a fluorescent dye, a radioisotope, a nuclide used for PET, a nuclide used for SPECT, an MRI contrast medium, a CT contrast medium, and a magnetic material. Preferred examples of the radioisotope, the nuclide used for PET, and the nuclide used for SPECT (single photon emission computed tomography) include $^{11}$C, $^{13}$N, $^{15}$O, $^{18}$F, $^{66}$Ga, $^{67}$Ga, $^{68}$Ga, $^{60}$Cu, $^{61}$Cu, $^{62}$Cu, $^{67}$Cu, $^{64}$Cu, $^{48}$V, Tc-99m, $^{241}$Am, $^{55}$Co, $^{57}$Co, $^{153}$Gd, $^{111}$In, $^{133}$Ba, $^{82}$Rb, $^{139}$Ce, Te-123m, $^{137}$Cs, $^{86}$Y, $^{90}$Y, $^{185/187}$Re, $^{186/188}$Re, $^{125}$I, a complex thereof, and a combination thereof. Examples of the MRI contrast medium, the CT contrast medium, and the magnetic material include gadolinium, Gd-DTPA, Gd-DTPA-BMA, Gd-HP-DO3A, iodine, iron, iron oxide, chromium, manganese, and a complex or chelate complex thereof. Moreover, examples of the fluorescent dye include a known quantum dot, indocyanine green, and a near-infrared fluorescent dye (Cy5.5, Cy7, AlexaFluoro, etc.).

When the targeting agent of the present invention is used as a drug delivery agent, it is possible to encapsulate a drug (a therapeutically effective ingredient) into the targeting agent of the present invention. The type of the drug used herein is not particularly limited. Since the targeting agent for tumor site of the present invention has excellent affinity for tumor tissues, any type of drug, which has activity on such tumor tissues, can be used. An antitumor substance is preferable. The specific type of such an antitumor substance is not particularly limited. Examples of the antitumor substance include alkylating agents, various types of antimetabolites, antitumor antibiotics, other antitumor agents, antitumor plant constituents, BRM (biological response modifiers), anti-angiogenic agents, cell adhesion inhibitors, matrix metalloproteinase inhibitors, and hormones.

More specifically, examples of the alkylating agents include: chloroethylamine alkylating agents such as nitrogen mustard, nitrogen mustard N-oxide, ifosfamide, melphalan, cyclophosphamide and chlorambucil; aziridine alkylating agents such as carboquone and thiotepa; epoxide alkylating agents such as dibromomannitol and dibromodulcitol; nitrosourea alkylating agents such as carmustine, lomustine, semustine, nimustine hydrochloride, chlorozotocin and ranimustine; sulfonic acid esters such as busulphan, improsulfan tosilate and piposulfan; dacarbazine; and procarbazine.

Examples of various types of antimetabolites include: purine antimetabolites such as 6-mercaptopurine, azathiopurine, 6-thioguanine and thioinosine; pyrimidine antimetabolites such as fluorouracil, tegafur, tegafur/uracil, a tegafur/gimeracil/oteracil potassium-containing agent, carmofur, doxifluridine, broxuridine, cytarabine and enocitabine; folate antimetabolites such as methotrexate and trimetrexate; and the salts or complexes thereof.

Examples of the antitumor antibiotics include: anthracycline antibiotics such as daunorubicin, aclarubicin, doxorubicin, pirarubicin and epirubicin; actinomycin antibiotics such as actinomycin D; chromomycin antibiotics such as chromomycin A3; mitomycin antibiotics such as mitomycin C; bleomycin antibiotics such as bleomycin and peplomycin; and the salts or complexes thereof.

Examples of the other antitumor agents include cisplatin, carboplatin, oxaliplatin, TAS-103, tamoxifen, L-asparaginase, acegatone, schizophyllan, picibanil, ubenimex, Krestin, and the salts or complexes thereof.

Examples of the antitumor plant constituents include: plant alkaloids such as camptothecin, vindesine, vincristine and vinblastine; epipodophyllotoxins such as etoposide and teniposide; and the salts or complexes thereof. Further examples include pipobroman, neocarzinostatin, and hydroxyurea.

Examples of the BRM include tumor necrosis factors, indomethacin, and the salts or complexes thereof.

Examples of the anti-angiogenic agents include a fumagillol derivative, and the salt or complex thereof.

Examples of the cell adhesion inhibitors include a substance having an RGD sequence, and the salt or complex thereof.

Examples of the matrix metalloproteinase inhibitors include marimastat, batimastat, and the salts or complexes thereof.

Examples of the hormones include hydrocortisone, dexamethasone, methylprednisolone, prednisolone, prasterone, betamethasone, triamcinolone, oxymetholone, nandrolone, methenolone, fosfestrol, ethinyl estradiol, chlormadinone, medroxyprogesterone, and the salts or complexes thereof.

Examples of the form of a drug include a low-molecular-weight compound, a peptide, a protein, an antibody, siRNA, and a gene.

Specific drugs are listed above. However, the drug used in the present invention is not limited to the above-listed drugs.

The targeting agent (e.g. an imaging agent, a drug delivery agent, etc.) of the present invention can be used for the diagnosis of tumor, the diagnosis of the therapeutic effects for tumor, the analysis of the morbidity of tumor, or the treatment of tumor.

Target diseases include various types of cancers and tumors. Diagnostic methods that can be applied in the present invention include PET, SPECT, CT, MRI, endoscopy, and use of a fluorescence detector.

The dose, the usage, and the dosage form of the targeting agent of the present invention can be appropriately determined depending on the purpose of use. For example, the targeting agent of the present invention can be directly administered to a desired site in a living body. Alternatively, it may be suspended in a liquid excipient such as an aqueous solvent (e.g., distilled water for injection, a physiological saline for injection, or a buffer with pH 5 to 8 (e.g., a phosphate or citrate buffer)) so as to be administered via injection, external application, or the like. In addition, it may be mixed with an adequate excipient to adapt the form of ointment, gel, cream, or the like, so as to be externally applied. That is, the administration route of the targeting agent of the present invention may be the oral route or the parenteral route (e.g., intravenous administration, intramuscular administration, subcutaneous administration, or intradermal administration). Examples of the dosage form include: oral administration agents such as tablets, powders, capsules, granules, extracts, and syrups; and parenteral administration agents such as parenteral injections (e.g., intravenous injections, intramuscular injections, subcutaneous injections, and intradermal injections).

The targeting agent of the present invention can be formulated into a medicament according to a method known to persons skilled in the art. For example, if liquid is used as a carrier for a medicament, the targeting agent of the present invention can be dissolved or dispersed in the liquid. Alternatively, if a powder is used as a carrier for a medicament, the targeting agent of the present invention can be mixed with or adsorbed on the powder. Further, if necessary, a pharmaceutically acceptable additive (e.g., a preservative, a stabilizer, an antioxidant, an excipient, a binder, a disintegrator, a wetting agent, a lubricant, a coloring agent, an aromatic agent, a corrigent, a coating, a suspending agent, an emulsifier, a dissolution adjuvant, a buffer, an isotonizing agent, a plasticizer, a surfactant, or a soothing agent) can be mixed therewith.

The applied dose of the carrier is not particularly limited. However, for example, it can be 10 μg/kg to 100 mg/kg, and preferably 100 μg/kg to 10 mg/kg per kg of body weight of a subject organism, to which it is to be administered.

Hereinafter, the present invention will be more specifically described in the following examples. However, these examples are not intended to limit the scope of the present invention.

EXAMPLES

As a recombinant gelatin, the following CBE3 (described in WO2008-103041) was prepared.
CBE3
Molecular weight: 51.6 kD
Structure: Gly-Ala-Pro[(Gly-X-Y)$_{63}$]$_3$Gly
Number of amino acids: 571
Number of RGD sequences: 12
Imino acid content: 33%
(Substantially 100% of amino acids form the Gly-X-Y repeat structure. The amino acid sequence of CBE3 does not contain serine, threonine, asparagine, tyrosine, and cysteine. CBE3 has an ERGD sequence.)
Isoelectric point: 9.34
Amino acid sequence (SEQ ID NO: 1 in the Sequence Listing) (This amino acid sequence corresponds to the amino acid sequence shown in SEQ ID NO: 3 in WO2008/103041. Note that "X" at the end was modified to "P.")

```
GAP(GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP)3G
```

In the Examples described below, CBE3 above used as a recombinant gelatin is indicated as "R-Gel," unless specified otherwise.

(1) Production of ICG-Containing PEGylated Liposome

NC21E (manufactured by NOF Corporation) and PEG-distearoyl phosphatidyl ethanolamine (manufactured by NOF Corporation; hereinafter referred to as PEG) were dissolved in 10 ml of chloroform placed in an eggplant-shaped flask, resulting in concentrations of 180 mM and 20 mM, respectively. Then, using an evaporator and a vacuum dryer, chloroform was distilled away under a reduced pressure, and a dried membrane was formed on the bottom of the flask. Thereafter, 10 ml of a 20 μM ICG (indocyanine green) aqueous solution serving as a water phase was added to this eggplant-shaped flask, and it was then warmed to 60° C. for 2 minutes in a constant temperature bath. Thereafter, it was intensively stirred using a Vortex mixer, so that the dried membrane was dissolved and dispersed in the water phase.

A polycarbonate filter with a pore diameter of 0.1 μm (manufactured by Whatman; Nucleopore Membrane) was equipped into a mini-extruder set (manufactured by Avanti), and a hot plate was then warmed, so that the temperature of a filter housing became 55° C. The entire water phase in the eggplant-shaped flask was placed in a syringe, and the filter was shuttled 10 times, so as to carried out an extrusion treatment. Thereafter, purification by gel filtration was carried out using a Sephadex G100 Gel, so as to remove ICG existing in the external water phase. The resultant was then concentrated by centrifugal ultrafiltration. The thus produced particles are defined as an ICG-containing PEGylated liposome. The particle diameter and ξ potential thereof were measured using ELS-Z2 (manufactured by Otsuka Electronics Co., Ltd.). The results are shown in Table 1.

TABLE 1

|  | ICG-containing PEGylated liposome |
|---|---|
| Particle diameter (nm) | 100.1 |
| ξ Potential (mV) | −53 |

(2) Production of R-Gel-Coated ICG-Containing PEGylated Liposome

A 0.5% R-Gel dissolved solution (solvent: PBS) was mixed with the ICG-containing PEGylated liposome prepared in (1) above at a volume ratio of 1:1, and the obtained mixture was then left at rest at 10° C. for 30 minutes, so as to produce an R-Gel-coated ICG-containing PEGylated liposome. The particle diameter and potential thereof were measured. The results are shown in Table 2. It was concluded that the PEGylated liposome was coated with R-Gel, based on the fact that the potential had been increased after addition of the R-Gel. Moreover, an animal gelatin (Nippi, Inc.; isoelectric point: 9; molecular weight: 53 kDa) was used as a control of the R-Gel in the same manner as that described above.

TABLE 2

|  | ICG-containing PEGylated liposome | After addition of R-Gel | After addition of animal gelatin |
|---|---|---|---|
| NC21E concentration (mM) |  | 180 |  |
| PEG concentration (mM) |  | 20 |  |
| Water phase ICG concentration (μM) |  | 200 |  |
| Particle diameter (nm) | 100.1 | 94.9 | 116.6 |
| ξ Potential (mV) | −53 | −16 | −14.7 |

(3) Production of Tumor-Bearing Animal Model

A cancer-bearing animal was produced as a tumor-bearing animal model. Kitayama Labes Co., Ltd. was entrusted to produce such a cancer-bearing animal. A BALB/cAJcl-nu/nu mouse (male, 5-week-old; CLEA Japan, Inc.) was used as an animal for production of the cancer-bearing animal. U-87MG (human glioblastoma) was used as cells to be transplanted into the mouse. The cells were cultured in an Eagle's Minimum Essential Medium containing 10% fetal bovine serum. For the culture, a T-225 flask was used. The thus obtained U-87MG cell solution ($5 \times 10^6$ cells/50 μl) was transplanted into the subcutis of the right flank of the BALB/cAJcl-nu/nu mouse. Two weeks after the transplantation, a tumor, which reached a size of 100 mm$^3$, was formed. This mouse was used as a cancer-bearing animal in the subsequent experiments. Hereinafter, this mouse is referred to as a cancer-bearing animal.

(4) Imaging of Tumor Site of Cancer-Bearing Animal Using R-Gel-Coated ICG-Containing PEGylated Liposome 100 μl of an R-Gel-coated ICG-containing PEGylated liposome, an animal gelatin-coated ICG-containing PEGylated liposome, or an ICG-containing PEGylated liposome was administered into the caudal vein of the cancer-bearing animal. Thereafter, a fluorescence imaging experiment was then performed ex vivo.

For detection of a fluorescence signal, measurement and imaging, Lumino image analyzer LAS5000 (a trial product of Fujifilm Corporation) was used. A visible light image and a fluorescence image were simultaneously taken, and the two images were then overlapped to identify a site from which fluorescence was emitted. In order to take such a fluorescence image, incident light-IR light source was used as a light source, and a 795-nm band-pass filter was used as a filter. For image analysis and the measurement of signal strength, software, MultiGauge (Fujifilm Corporation) was used.

As a result, it was confirmed that, six hours after the administration, only in the case of the R-Gel-coated ICG-containing PEGylated liposome, fluorescence was accumulated in the tumoral neovascular site and tumor site of the cancer-bearing animal (FIG. 1).

Comparative Example

GLYCOLIPO K Series, K1-Cy7, which was a fluorescent dye Cy7-containing liposome purchased from Katayama Chemical, Ltd., was used as a comparative example. The particle diameter and ξ potential thereof, which were described in the certificate of analysis, are shown in Table 3.

TABLE 3

|  | K1-Cy7 |
|---|---|
| Particle diameter (nm) | 93 |
| ξ Potential (mV) | −59 |

Imaging of Tumor Site of Cancer-Bearing Animal by K1-Cy7

100 μl of K1-Cy7 was administered into the caudal vein of a cancer-bearing animal, and a fluorescence imaging experiment was then performed ex vivo in the same manner as that of the previous experiment.

As a result, accumulation of fluorescence was not confirmed in the tumoral neovascular site and tumor site of the cancer-bearing animal until six hours after the administration of K1-Cy7 in the above experimental system. Thus, it was found that K1-Cy7 has accumulation ability that is inferior to that of the targeting agent of the present invention.

It is anticipated that, in principle, the same result as described above will be obtained from a DDS carrier whose surface is modified by a hydrophilic polymer, such as a polymer micelle.

The invention claimed is:

1. A method for targeting a labeled probe and/or drug to a tumor site, which comprises administering to a living body, a hydrophilic polymer-modified carrier which is coated with a gelatin-like protein that has repeats of a sequence represented by Gly-X-Y characteristic to collagen and has two or more sequences of cell adhesion signals in a single molecule wherein X and Y each independently represents an amino acid and a plurality of Gly-X-Y sequences may be the same or different, wherein the carrier further comprises the labeled probe and/or the drug, and targeting the labeled probe and/or the drug to the tumor site by the function of the gelatin-like protein.

2. The method according to claim 1, wherein the hydrophilic polymer-modified carrier is a liposome containing a lipid membrane component modified with a hydrophilic polymer, or a polymer micelle modified with a hydrophilic polymer.

3. The method according to claim 1, wherein the molecular weight of the gelatin-like protein is 2 KDa to 100 KDa.

4. The method according to claim 1, wherein the gelatin-like protein is represented by the formula:

A-[(Gly-X-Y)$_n$]$_m$-B wherein A represents any amino acid or amino acid sequence, B represents any amino acid or amino acid sequence, there exist n amino acids each independently represented by X, there exist n amino acids each independently represented by Y, n represents an integer from 3 to 100, m represents an integer of 2 to 10, and n Gly-X-Y sequences may be the same or different.

5. The method according to claim 1, wherein the gelatin-like protein is represented by the formula:

Gly-Ala-Pro-[(Gly-X-Y)$_{63}$]$_3$-Gly wherein there exist 63 amino acids each independently represented by X, there exist 63 amino acids each independently represented by Y, and 63 Gly-X-Y sequences may be the same or different.

6. The method according to claim 1, wherein the cell adhesion signal is an amino acid sequence represented by Arg-Gly-Asp.

7. The method according to claim 1, wherein the amino acid sequence of the gelatin-like protein does not comprise any of serine and threonine.

8. The method according to claim 1, wherein the amino acid sequence of the gelatin-like protein does not comprise any of serine, threonine, asparagine, tyrosine and cysteine.

9. The method according to claim 1, wherein the amino acid sequence of the gelatin-like protein does not comprise an amino acid sequence represented by Asp-Arg-Gly-Asp.

10. The method according to claim 1, wherein the gelatin-like protein has (1) the amino acid sequence shown in SEQ ID NO: 1, or (2) an amino acid sequence having 80% or more homology to the amino acid sequence shown in SEQ ID NO: 1 and having targeting activity on a tumor site.

11. The method according to claim 1, wherein the gelatin-like protein is crosslinked.

12. The method according to claim 1, wherein the crosslinking is carried out using an aldehyde, a condensing agent or an enzyme.

13. The method according to claim 1, wherein the hydrophilic polymer is polyethylene glycol.

14. The method according to claim 1, wherein the labeled probe is a fluorescent dye, a radioisotope, a nuclide used for PET, a nuclide used for SPECT, an MRI contrast medium, a CT contrast medium, or a magnetic material.

15. The method according to claim 14, wherein the fluorescent dye is a quantum dot, indocyanine green, or a near-infrared fluorescent dye; each of the radioisotope, the nuclide used for PET, and the nuclide used for SPECT is $^{11}$C, $^{13}$N, $^{15}$O, $^{18}$F, $^{66}$Ga, $^{67}$Ga, $^{68}$Ga, $^{60}$Cu, $^{61}$Cu, $^{62}$Cu, $^{67}$Cu, $^{64}$Cu, $^{48}$V, Tc-99m, $^{241}$Am, $^{55}$Co, $^{57}$Co, $^{153}$Gd, $^{111}$In, $^{133}$Ba, $^{82}$Rb, $^{139}$Ce, Te-123m, $^{137}$Cs, $^{86}$Y, $^{90}$Y, $^{185/187}$Re, $^{125}$I, or a complex thereof, or a combination thereof; and each of the MRI contrast medium, the CT contrast medium, and the magnetic material is gadolinium, Gd-DTPA, Gd-DTPA-BMA, Gd-HP-DO3A, iodine, iron, iron oxide, chromium, manganese, a complex or chelate complex thereof, or a combination thereof.

* * * * *